(12) United States Patent
Tallent et al.

(10) Patent No.: US 10,115,291 B2
(45) Date of Patent: Oct. 30, 2018

(54) LOCATION-BASED INCONTINENCE DETECTION

(71) Applicant: Hill-Rom Services, Inc., Batesville, IN (US)

(72) Inventors: Dan R. Tallent, Hope, IN (US); Gavin M. Monson, Oxford, OH (US); James D. Voll, Columbus, IN (US); Victor Potter, Middletown, OH (US)

(73) Assignee: Hill-Rom Services, Inc., Batesville, IN (US)

( * ) Notice: Subject to any disclaimer, the term of this patent is extended or adjusted under 35 U.S.C. 154(b) by 0 days.

(21) Appl. No.: 15/490,109

(22) Filed: Apr. 18, 2017

(65) Prior Publication Data
US 2017/0309155 A1 Oct. 26, 2017

Related U.S. Application Data (60) Provisional application No. 62/327,627, filed on Apr. 26, 2016.

(51) Int. Cl.
| | |
|---|---|
| *G08B 21/20* | (2006.01) |
| *G06K 19/07* | (2006.01) |
| *A61F 13/42* | (2006.01) |
| *A61F 13/44* | (2006.01) |
| *G08B 21/18* | (2006.01) |
| *A61G 7/057* | (2006.01) |
| *A61B 5/11* | (2006.01) |
| *A61B 5/20* | (2006.01) |
| *G06F 19/00* | (2018.01) |

(Continued)

(52) U.S. Cl.
CPC ............ *G08B 21/20* (2013.01); *A61B 5/0002* (2013.01); *A61B 5/1113* (2013.01); *A61B 5/202* (2013.01); *A61B 5/7495* (2013.01); *A61F 13/42* (2013.01); *A61F 13/44* (2013.01); *A61G 7/057* (2013.01); *G06F 19/00* (2013.01); *G06K 19/07* (2013.01); *G08B 21/182* (2013.01); *A61B 5/6892* (2013.01); *A61B 2560/0214* (2013.01); *A61B 2562/029* (2013.01); *A61B 2562/08* (2013.01); *A61G 2203/30* (2013.01); *A61G 2205/60* (2013.01); *G16H 10/65* (2018.01)

(58) Field of Classification Search
None
See application file for complete search history.

(56) References Cited

U.S. PATENT DOCUMENTS

| | | | |
|---|---|---|---|
| 1,772,232 | A | 8/1930 | Guilder |
| 2,127,538 | A | 8/1938 | Seiger |

(Continued)

FOREIGN PATENT DOCUMENTS

| | | |
|---|---|---|
| CA | 2361145 A1 | 12/1999 |
| CA | 2494896 A1 | 12/1999 |

(Continued)

OTHER PUBLICATIONS

European Search Report dated Oct. 2, 2017 for European Patent Application No. 17167606.7, 8 pages.

*Primary Examiner* — Laura Nguyen
(74) *Attorney, Agent, or Firm* — Barnes & Thornburg LLP (57) ABSTRACT

The present disclosure include devices, systems, and methods for location-based incontinence detection and monitoring including a communication device receiving incontinence event indicators occurrence and location indicators.

22 Claims, 3 Drawing Sheets

US 10,115,291 B2
Page 2

(51) Int. Cl.
*A61B 5/00* (2006.01)
*G16H 10/65* (2018.01)

(56) References Cited

U.S. PATENT DOCUMENTS

| | | | |
|---|---|---|---|
| 2,644,050 A | 6/1953 | Seiger |
| 2,668,202 A | 2/1954 | Kaplan |
| 2,726,294 A | 12/1955 | Kroening et al. |
| 2,907,841 A | 10/1959 | Campbell |
| 3,199,095 A | 8/1965 | Ashida |
| 3,971,371 A | 7/1976 | Bloom |
| 4,069,817 A | 1/1978 | Fenote et al. |
| 4,106,001 A | 8/1978 | Mahoney |
| 4,163,449 A | 8/1979 | Regal |
| 4,191,950 A | 3/1980 | Levin et al. |
| 4,212,295 A | 7/1980 | Snyder |
| 4,228,426 A | 10/1980 | Roberts |
| 4,347,503 A | 8/1982 | Uyehara |
| 4,539,559 A | 9/1985 | Kelley et al. |
| 4,747,166 A | 5/1988 | Kuntz |
| 4,965,554 A | 10/1990 | Darling |
| 5,081,422 A | 1/1992 | Shih |
| 5,086,294 A | 2/1992 | Schwab, Jr. |
| 5,137,033 A | 8/1992 | Norton |
| 5,144,284 A | 9/1992 | Hammett |
| 5,291,181 A | 3/1994 | De Ponte |
| 5,438,721 A | 8/1995 | Pahno et al. |
| 5,459,452 A | 10/1995 | DePonte |
| 5,491,609 A | 2/1996 | Dankman et al. |
| 5,537,095 A | 7/1996 | Dick et al. |
| 5,675,854 A | 10/1997 | Zibetin |
| 5,760,694 A | 6/1998 | Nissim et al. |
| 5,790,035 A | 8/1998 | Ho |
| 5,824,883 A | 10/1998 | Park et al. |
| 5,910,080 A | 6/1999 | Selton |
| 5,947,943 A | 9/1999 | Lee |
| 5,949,332 A * | 9/1999 | Kim ............... G08B 25/10 340/287 |
| 6,028,241 A | 2/2000 | Armstead |
| 6,047,419 A | 4/2000 | Fergusaon |
| 6,104,311 A | 8/2000 | Lastinger |
| 6,292,102 B1 | 9/2001 | Smith |
| 6,340,932 B1 | 1/2002 | Rodgers et al. |
| 6,341,393 B1 | 1/2002 | Votel |
| 6,351,215 B2 | 2/2002 | Rodgers et al. |
| 6,362,737 B1 | 3/2002 | Rodgers et al. |
| 6,384,728 B1 | 5/2002 | Kanor et al. |
| 6,544,200 B1 | 4/2003 | Smith et al. |
| 6,552,661 B1 | 4/2003 | Lastinger et al. |
| 6,583,722 B2 | 6/2003 | Jeutter et al. |
| 6,603,403 B2 | 8/2003 | Jeutter et al. |
| 6,621,410 B1 | 9/2003 | Lastinger et al. |
| 6,774,800 B2 | 8/2004 | Friedman et al. |
| 6,831,562 B2 | 12/2004 | Rodgers et al. |
| 6,832,507 B1 | 12/2004 | van de Berg et al. |
| 6,933,849 B2 | 8/2005 | Sawyer |
| 6,948,205 B2 | 9/2005 | Van Der Wurf et al. |
| 6,982,646 B2 | 1/2006 | Rodgers et al. |
| 7,017,213 B2 | 3/2006 | Chisari |
| 7,030,731 B2 | 4/2006 | Lastinger et al. |
| 7,071,830 B2 | 7/2006 | Sahlberg et al. |
| 7,120,952 B1 | 10/2006 | Bass et al. |
| 7,181,206 B2 | 2/2007 | Pedersen |
| 7,250,547 B1 | 7/2007 | Hofmeister et al. |
| 7,253,729 B2 | 8/2007 | Lastinger et al. |
| 7,274,944 B2 | 9/2007 | Lastinger et al. |
| 7,302,278 B2 | 11/2007 | Lastinger et al. |
| 7,305,246 B2 | 12/2007 | Lastinger et al. |
| 7,308,270 B2 | 12/2007 | Lastinger et al. |
| 7,348,930 B2 | 3/2008 | Lastinger et al. |
| 7,349,701 B2 | 3/2008 | Lastinger et al. |
| 7,355,090 B2 | 4/2008 | Ales, III et al. |
| 7,359,675 B2 | 4/2008 | Lastinger et al. |
| 7,400,860 B2 | 7/2008 | Lastinger et al. |
| 7,424,298 B2 | 9/2008 | Lastinger et al. |
| 7,489,252 B2 | 2/2009 | Long et al. |
| 7,489,282 B2 | 2/2009 | Lastinger et al. |
| 7,498,478 B2 | 3/2009 | Long et al. |
| 7,551,089 B2 | 6/2009 | Sawyer |
| 7,586,385 B2 | 9/2009 | Rokhsaz |
| 7,595,734 B2 | 9/2009 | Long et al. |
| 7,595,756 B2 | 9/2009 | Lastinger et al. |
| 7,598,853 B2 | 10/2009 | Becker et al. |
| 7,598,862 B2 | 10/2009 | Lastinger et al. |
| 7,599,699 B2 | 10/2009 | Lastinger et al. |
| 7,616,959 B2 | 11/2009 | Spenik et al. |
| 7,633,378 B2 | 12/2009 | Rodgers et al. |
| 7,649,125 B2 | 1/2010 | Ales, III et al. |
| 7,663,483 B2 | 2/2010 | Spenik et al. |
| 7,667,600 B2 | 2/2010 | Woodbury et al. |
| 7,812,731 B2 | 10/2010 | Bunza et al. |
| 7,822,386 B2 | 10/2010 | Lastinger et al. |
| 7,834,234 B2 | 11/2010 | Roe et al. |
| 7,834,235 B2 | 11/2010 | Long et al. |
| 7,834,765 B2 | 11/2010 | Sawyer |
| 7,834,766 B2 | 11/2010 | Sawyer |
| 7,838,720 B2 | 11/2010 | Roe et al. |
| 7,849,544 B2 | 12/2010 | Flocard et al. |
| 7,873,319 B2 | 1/2011 | Lastinger et al. |
| 7,977,529 B2 | 7/2011 | Bergman et al. |
| 8,009,646 B2 | 8/2011 | Lastinger et al. |
| 8,073,386 B2 | 12/2011 | Pedersen |
| 8,081,043 B2 | 12/2011 | Rokhsaz |
| 8,102,254 B2 | 1/2012 | Becker et al. |
| 8,104,126 B2 | 1/2012 | Caminade et al. |
| 8,106,782 B2 | 1/2012 | Fredriksson et al. |
| 8,111,165 B2 | 2/2012 | Ortega et al. |
| 8,111,678 B2 | 2/2012 | Lastinger et al. |
| 8,121,856 B2 | 2/2012 | Huster et al. |
| 8,181,290 B2 | 5/2012 | Brykalski et al. |
| 8,191,187 B2 | 6/2012 | Brykalski et al. |
| 8,196,809 B2 | 6/2012 | Thorstensson |
| 8,237,572 B2 | 8/2012 | Clement et al. |
| 8,248,249 B2 | 8/2012 | Clement et al. |
| 8,270,383 B2 | 8/2012 | Lastinger et al. |
| 8,279,069 B2 | 10/2012 | Sawyer |
| 8,319,633 B2 | 11/2012 | Becker et al. |
| 8,325,695 B2 | 12/2012 | Lastinger et al. |
| 8,332,975 B2 | 12/2012 | Brykalski et al. |
| 8,345,651 B2 | 1/2013 | Lastinger et al. |
| 8,395,014 B2 | 3/2013 | Helmer et al. |
| 8,428,039 B2 | 4/2013 | Lastinger et al. |
| 8,428,605 B2 | 4/2013 | Pedersen et al. |
| 8,461,982 B2 | 6/2013 | Becker et al. |
| 8,482,305 B2 | 7/2013 | Johnson |
| 8,487,774 B2 | 7/2013 | Reeder et al. |
| 8,502,684 B2 | 8/2013 | Bunza et al. |
| 8,628,506 B2 | 1/2014 | Ales, III et al. |
| 8,674,826 B2 | 3/2014 | Becker et al. |
| 8,742,929 B2 | 6/2014 | Sawyer |
| 8,749,319 B2 | 6/2014 | Rokhsaz et al. |
| 8,766,804 B2 | 7/2014 | Reeder et al. |
| 8,842,013 B2 | 9/2014 | Sawyer |
| 8,855,089 B2 | 10/2014 | Lastinger et al. |
| 8,866,615 B2 | 10/2014 | Sawyer |
| 8,878,557 B2 | 11/2014 | Kristiansen et al. |
| 8,878,676 B2 | 11/2014 | Koblasz |
| 8,896,449 B2 | 11/2014 | Sawyer |
| 8,914,923 B2 | 12/2014 | Smith |
| 8,933,292 B2 | 1/2015 | Abraham et al. |
| 8,962,909 B2 | 2/2015 | Groosman et al. |
| 9,048,819 B2 | 6/2015 | Rokhsaz et al. |
| 9,107,776 B2 | 8/2015 | Bergman et al. |
| 2002/0002633 A1 * | 1/2002 | Colling, III ............. G06F 9/542 719/318 |
| 2002/0011932 A1 | 1/2002 | Rodgers et al. |
| 2002/0033757 A1 | 3/2002 | Rodgers et al. |
| 2002/0145526 A1 | 10/2002 | Friedman et al. |
| 2003/0030568 A1 | 2/2003 | Lastinger et al. |
| 2005/0003763 A1 | 1/2005 | Lastinger et al. |
| 2005/0003865 A1 | 1/2005 | Lastinger et al. |
| 2005/0052282 A1 | 3/2005 | Rodgers et al. |
| 2005/0060246 A1 | 3/2005 | Lastinger et al. |
| 2005/0099294 A1 | 5/2005 | Bogner et al. |

(56) References Cited

U.S. PATENT DOCUMENTS

| | | |
|---|---|---|
| 2005/0242946 A1 | 11/2005 | Hubbard, Jr. et al. |
| 2005/0250453 A1 | 11/2005 | Lastinger et al. |
| 2005/0277441 A1 | 12/2005 | Lastinger et al. |
| 2005/0282545 A1 | 12/2005 | Lastinger et al. |
| 2005/0282553 A1 | 12/2005 | Lastinger et al. |
| 2006/0164320 A1 | 7/2006 | Lastinger et al. |
| 2006/0270351 A1 | 11/2006 | Lastinger et al. |
| 2006/0279427 A1* | 12/2006 | Becker .................. A61B 5/0002 340/573.4 |
| 2007/0159332 A1 | 7/2007 | Koblasz |
| 2007/0202809 A1 | 8/2007 | Lastinger et al. |
| 2007/0270774 A1 | 11/2007 | Bergman et al. |
| 2008/0116990 A1 | 5/2008 | Rokhsaz |
| 2008/0204245 A1 | 8/2008 | Blair et al. |
| 2008/0262376 A1 | 10/2008 | Price |
| 2008/0263776 A1 | 10/2008 | O'Reagan et al. |
| 2009/0160648 A1 | 6/2009 | Rokhsaz |
| 2009/0289743 A1 | 11/2009 | Rokhsaz |
| 2009/0292265 A1 | 11/2009 | Helmer et al. |
| 2009/0315728 A1 | 12/2009 | Ales, III et al. |
| 2009/0326417 A1 | 12/2009 | Ales, III et al. |
| 2010/0043143 A1 | 2/2010 | O'Reagan et al. |
| 2010/0072271 A1 | 3/2010 | Thorstensson |
| 2011/0025458 A1 | 2/2011 | Rokhsaz et al. |
| 2011/0025473 A1 | 2/2011 | Rokhsaz et al. |
| 2011/0092890 A1 | 4/2011 | Stryker et al. |
| 2011/0115635 A1 | 5/2011 | Petrovski et al. |
| 2011/0263952 A1 | 10/2011 | Bergman et al. |
| 2011/0283459 A1 | 11/2011 | Essers |
| 2011/0291810 A1 | 12/2011 | Rokhsaz et al. |
| 2011/0295619 A1 | 12/2011 | Tough |
| 2011/0300808 A1 | 12/2011 | Rokhsaz et al. |
| 2011/0302720 A1 | 12/2011 | Yakam et al. |
| 2011/0309937 A1 | 12/2011 | Bunza et al. |
| 2012/0092027 A1 | 4/2012 | Forster |
| 2012/0119912 A1 | 5/2012 | Ortega et al. |
| 2012/0119915 A1 | 5/2012 | Clement et al. |
| 2012/0130330 A1 | 5/2012 | Wilson et al. |
| 2012/0165772 A1 | 6/2012 | Groosman et al. |
| 2012/0217311 A1 | 8/2012 | Rokhsaz et al. |
| 2012/0268278 A1 | 10/2012 | Lewis et al. |
| 2013/0079590 A1 | 3/2013 | Bengtson |
| 2013/0109929 A1 | 5/2013 | Menzel |
| 2013/0123726 A1 | 5/2013 | Yu et al. |
| 2013/0189946 A1* | 7/2013 | Swanson ............ H04W 64/006 455/404.2 |
| 2013/0254141 A1 | 9/2013 | Barda et al. |
| 2014/0070950 A1 | 3/2014 | Snodgrass |
| 2014/0120836 A1 | 5/2014 | Rokhsaz et al. |
| 2014/0148772 A1 | 5/2014 | Hu et al. |
| 2014/0152442 A1 | 6/2014 | Li |
| 2014/0200538 A1 | 7/2014 | Euliano et al. |
| 2014/0236629 A1 | 8/2014 | Kim et al. |
| 2014/0244644 A1 | 8/2014 | Mashinchi et al. |
| 2014/0247125 A1 | 9/2014 | Barsky |
| 2014/0266735 A1 | 9/2014 | Riggio et al. |
| 2014/0296808 A1 | 10/2014 | Curran et al. |
| 2014/0358099 A1 | 12/2014 | Durgin et al. |
| 2015/0076221 A1* | 3/2015 | Rushing .................. G01C 15/04 235/375 |
| 2015/0080819 A1 | 3/2015 | Charna et al. |
| 2015/0080834 A1 | 3/2015 | Mills |
| 2015/0087935 A1 | 3/2015 | Davis et al. |
| 2015/0164438 A1 | 6/2015 | Halperin et al. |
| 2016/0157755 A1* | 6/2016 | Becker .................. A61B 5/1115 340/573.4 |
| 2017/0098044 A1* | 4/2017 | Lai ...................... G06K 19/0716 |

FOREIGN PATENT DOCUMENTS

| | | |
|---|---|---|
| CN | 102568259 A | 7/2012 |
| CN | 202711437 U | 1/2013 |
| CN | 102985853 A | 3/2013 |
| DE | 4137631 A | 5/1992 |
| DE | 69906388 T2 | 2/2004 |
| DE | 69915370 T2 | 3/2005 |
| DE | 69917491 T2 | 5/2005 |
| DE | 60016946 T2 | 6/2006 |
| DE | 102007050074 A1 | 4/2009 |
| EP | 0335279 A1 | 10/1989 |
| EP | 1286179 A2 | 12/1999 |
| EP | 1147603 A2 | 10/2001 |
| EP | 1149305 A2 | 10/2001 |
| EP | 1153317 A2 | 11/2001 |
| EP | 1218771 A2 | 7/2002 |
| EP | 1153317 B1 | 3/2003 |
| EP | 1147603 B1 | 3/2004 |
| EP | 1410353 A2 | 4/2004 |
| EP | 1149305 B1 | 5/2004 |
| EP | 1218771 B1 | 12/2004 |
| EP | 1684615 A1 | 8/2006 |
| EP | 2014267 A1 | 6/2007 |
| EP | 1868553 A1 | 12/2007 |
| EP | 1897278 A1 | 3/2008 |
| EP | 1959900 A1 | 8/2008 |
| EP | 1994650 A2 | 11/2008 |
| EP | 2019659 A1 | 2/2009 |
| EP | 1410353 B1 | 12/2009 |
| EP | 1897278 B1 | 1/2010 |
| EP | 1684615 B1 | 2/2010 |
| EP | 2156222 A1 | 2/2010 |
| EP | 2313044 A2 | 4/2011 |
| EP | 2579069 A2 | 6/2011 |
| EP | 2444039 A1 | 8/2011 |
| EP | 1959900 B1 | 2/2012 |
| EP | 2738748 A1 | 4/2012 |
| EP | 2452183 A1 | 5/2012 |
| EP | 2496197 A1 | 9/2012 |
| EP | 1994650 B1 | 12/2012 |
| EP | 2542200 A1 | 1/2013 |
| EP | 2582341 A1 | 4/2013 |
| EP | 2729107 A1 | 5/2014 |
| EP | 2739254 A1 | 6/2014 |
| EP | 2156222 B1 | 8/2015 |
| EP | 2739254 B1 | 11/2016 |
| GB | 145859 | 3/1919 |
| GB | 2145859 | 4/1985 |
| GB | 2408204 A | 11/2003 |
| WO | WO 89/10110 A1 | 4/1989 |
| WO | WO 94/20002 A1 | 3/1994 |
| WO | WO 00/44091 A2 | 7/2000 |
| WO | WO 01/25817 A2 | 4/2001 |
| WO | WO 01/85085 A2 | 11/2001 |
| WO | WO 02/103645 A2 | 12/2002 |
| WO | WO 2006/108540 A1 | 10/2006 |
| WO | WO 2007/069968 A1 | 6/2007 |
| WO | WO 2008/130298 A1 | 10/2008 |
| WO | 2010001271 A2 | 1/2010 |
| WO | WO 2010/001271 A3 | 1/2010 |
| WO | WO 2010/043368 A1 | 4/2010 |
| WO | 2011107580 A1 | 9/2011 |
| WO | WO 2011/107580 A1 | 9/2011 |
| WO | 2012136157 A1 | 10/2012 |
| WO | WO 2012/136157 A1 | 10/2012 |
| WO | WO 2014/165041 | 10/2014 |
| WO | WO 2015/137999 | 9/2015 |

* cited by examiner

LOCATION-BASED INCONTINENCE DETECTION

The present application claims the benefit, under 35 U.S.C. § 119(e), of U.S. Provisional Application No. 62/327,627, which was filed Apr. 26, 2016, and which is hereby incorporated by reference herein in its entirety.

FIELD

The present disclosure relates to devices, systems, and methods for managing patients of care facilities. More specifically, devices, systems, and methods for detecting incontinence events of patients of care facilities.

BACKGROUND

Patients of care facilities, such as hospitals, may experience incontinence events. In addition to hygiene concerns, such incontinence events generally expose a patient to excessive moisture. Exposure to excessive moisture can have a negative impact on patient care conditions, for example, by increasing the risk and/or severity of bed sores and other mobility related complications. Some of the risks related to incontinence events can be reduced by cleaning and/or removing soiled materials from contact with a patient's skin in a timely manner to reduce the duration and/or severity of the exposure.

SUMMARY

The present application discloses one or more of the features recited in the appended claims and/or the following features which, alone or in any combination, may comprise patentable subject matter:

According to an aspect of the disclosure, an incontinence detection system may include a patient bed and an incontinence detection device that may be positioned on the patient bed to detect incontinence events. The incontinence detection device may include a sensor adapted to sense the presence of a threshold amount of moisture on the patient bed and to communicate a detection signal that may indicate the presence of the threshold amount of moisture and an RFID-incontinence transmitter that may be in communication with the sensor and that may be adapted to send an incontinence RFID signal that may indicate that the threshold amount of moisture has been sensed in response to the detection signal. The system may further have an RFID-location transmitter that may be fixed relative to the patient bed and that may be configured to send a location RFID signal indicating a unique location identifier. The system may further have an RFID reader that may be configured to receive the incontinence RFID signal and the location RFID signal, and to communicate the occurrence of an incontinence event and the unique location identifier in response to receiving the incontinence RFID signal and the location RFID signal.

In some embodiments, the RFID reader may be configured to generate a communications signal that may indicate both the occurrence of an incontinence event and the unique location identifier to remote devices. The RFID-incontinence transmitter may include a passive RFID device, for example. The passive RFID device may receive excitation from the RFID reader to power the RFID-incontinence transmitter. The RFID reader may be configured to transmit excitation signals at regular intervals to the RFID-incontinence transmitter to power the RFID-incontinence transmitter.

In some embodiments, the RFID-location transmitter may include an active RFID device. The active RFID device may include a power source that may include a photovoltaic cell. The RFID reader may be attached to the patient bed, for example. The incontinence device may include a removable and replaceable pad.

According to another aspect of the present disclosure, an incontinence detection system may include an incontinence detection device for detecting incontinence events. The incontinence detection device may include an incontinence pad and an RFID-incontinence transmitter. The incontinence pad may include at least one sensor that may be adapted to sense the presence of moisture and to communicate a detection signal indicating the presence of moisture to the RFID-incontinence transmitter. The RFID-incontinence transmitter may be adapted to send an incontinence RFID signal indicating that moisture has been sensed in response to receiving the detection signal. The system may include an RFID-location transmitter that may be fixed relative to the patient bed and that may be configured to send a location RFID signal that may indicate a unique location identifier. The system may further have an RFID reader that may be configured to receive the incontinence RFID signal and the location RFID signal, and that may be configured send a communication signal, in response to receiving the incontinence RFID signal and the location RFID signal, that may indicate the occurrence of an incontinence event and the unique location identifier.

In some embodiments, the RFID-incontinence transmitter may include a passive RFID device. The passive RFID device may receive excitation from the RFID reader to power the RFID-incontinence transmitter. The RFID reader may be configured to transmit excitation signals at regular intervals to the RFID-incontinence transmitter to power the RFID-incontinence transmitter.

In some embodiments, the RFID-location transmitter may include an active RFID device. The active RFID device may include a power source that may include a photovoltaic cell. The RFID reader may be attached to the patient support device. The incontinence pad may include a removable and replaceable pad.

According to a further aspect of the present disclosure, a method of detecting an incontinence event on a patient support device having an RFID reader may be provided. The method may include receiving with the RFID reader a location RFID signal that may indicate a unique location identifier, receiving with the RFID reader an incontinence RFID signal that may indicate the presence of moisture of the patient support device, and in response to receiving the incontinence RFID signal, generating a communications signal that may indicate the occurrence of an incontinence event and the unique location identifier.

In some embodiments, receiving with the RFID reader a location RFID signal that may indicate a unique location identifier may include storing the unique location identifier, and generating a communications signal may include retrieving the unique location identifier in response to receiving the incontinence RFID signal. In some embodiments, receiving at least one excitation signal for powering a passive RFID transmitter may include receiving an excitation signal from the RFID reader at regular intervals.

Additional features alone or in combination with any other feature(s), including those listed above and those listed in the claims and those described in detail below, may comprise patentable subject matter. Others will become apparent to those skilled in the art upon consideration of the following detailed description of illustrative embodiments exemplifying the best mode of carrying out the invention as presently perceived.

BRIEF DESCRIPTION OF THE DRAWINGS

The detailed description particularly refers to the accompanying figures in which.

DETAILED DESCRIPTION OF THE DRAWINGS

Patient incontinence events can increase the risk of bed sores and other complications common to mobility-restricted persons. Reducing a patient's exposure to incontinence events can reduce the potential for related complications. However, in a care facility (such as a hospital) that may care for many patients simultaneously, it can be challenging to detect and/or monitor patients for incontinence events. These challenges can be particularly important to patients with reduced mobility who may depend more intensely on hospital staff to remediate incontinence events. The present disclosure includes devices, systems, and methods for location-based incontinence detection and monitoring that can alert caregivers to the occurrence and location of incontinence events to assist in managing patients and can be easily and effectively retrofitted into existing care facilities and/or patient support devices.

Figure 1:
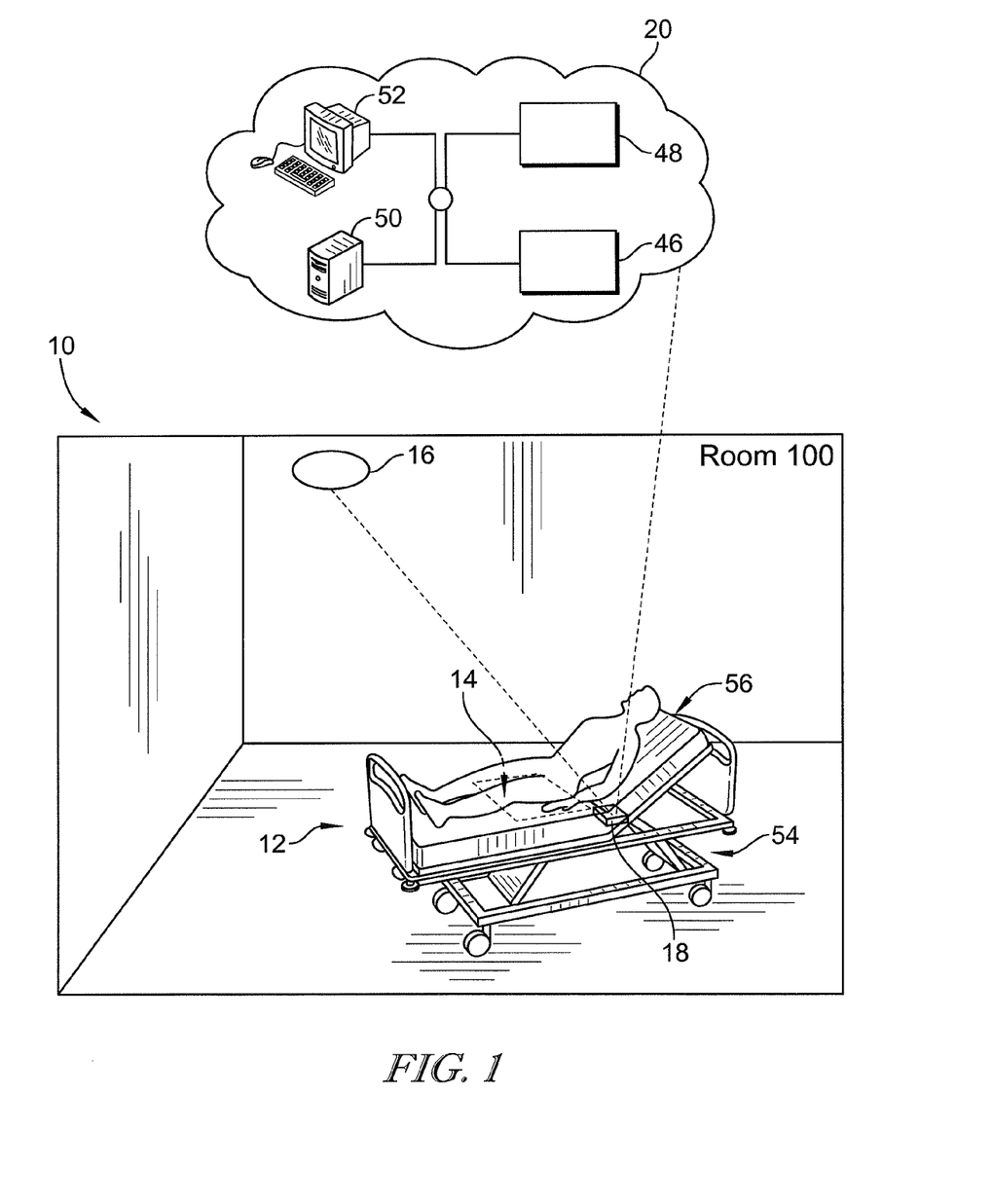
FIG. 1 is a perspective view of an incontinence detection system located within a room of a care facility showing that the incontinence detection system includes a communications device (embodied as an RFID reader) that is attached to a patient bed and is in communication with each of an incontinence detection device (in phantom) that is positioned on the bed and a location transmitter of the room to receive indications of the occurrence of incontinence events and location identifying information.

An illustrative embodiment of an incontinence detection system 10 located within a room 100 of a care facility is shown in FIG. 1. The incontinence detection system 10 illustratively includes a patient support device 12 embodied as a patient bed, an incontinence detection device 14 embodied as an incontinence pad installed on the bed 12, a location transmitter 16, and a communication device 18 for receiving information from the incontinence detection device 14 and the location transmitter 16. In the illustrative embodiment, the communication device 18 is embodied as an RFID reader, also known as an interrogator, configured to communicate wirelessly (through radio frequency (RF) signals) with each of the incontinence detection device 14 and the location transmitter 16 to receive indication of incontinence events and location identifiers for communication to caregivers.

The RFID reader 18 illustratively communicates with a network 20 of the care facility as shown in FIG. 1. The RFID reader 18 illustratively sends a signal to the network 20 indicating the occurrence and location of an incontinence event as communicated by the incontinence detection device 14 and the location transmitter 16, respectively. Thus, caregivers can be timely alerted to the occurrence and location of incontinence events, even at remote locations, via the network 20.

As shown in FIG. 1, the patient bed 12 illustratively includes a frame 54 and a mattress 56 supported above the floor by the frame 54. In the illustrative embodiment, the incontinence detection device 14 is positioned on top of the mattress 56 and beneath the bed linens, and the RFID reader 18 is illustratively attached to the frame 54. In some embodiments, the RFID reader 18 may be located in any suitable position for communication with each of the incontinence detection device 14, the location transmitter 18, and the network 20.

Figure 2:
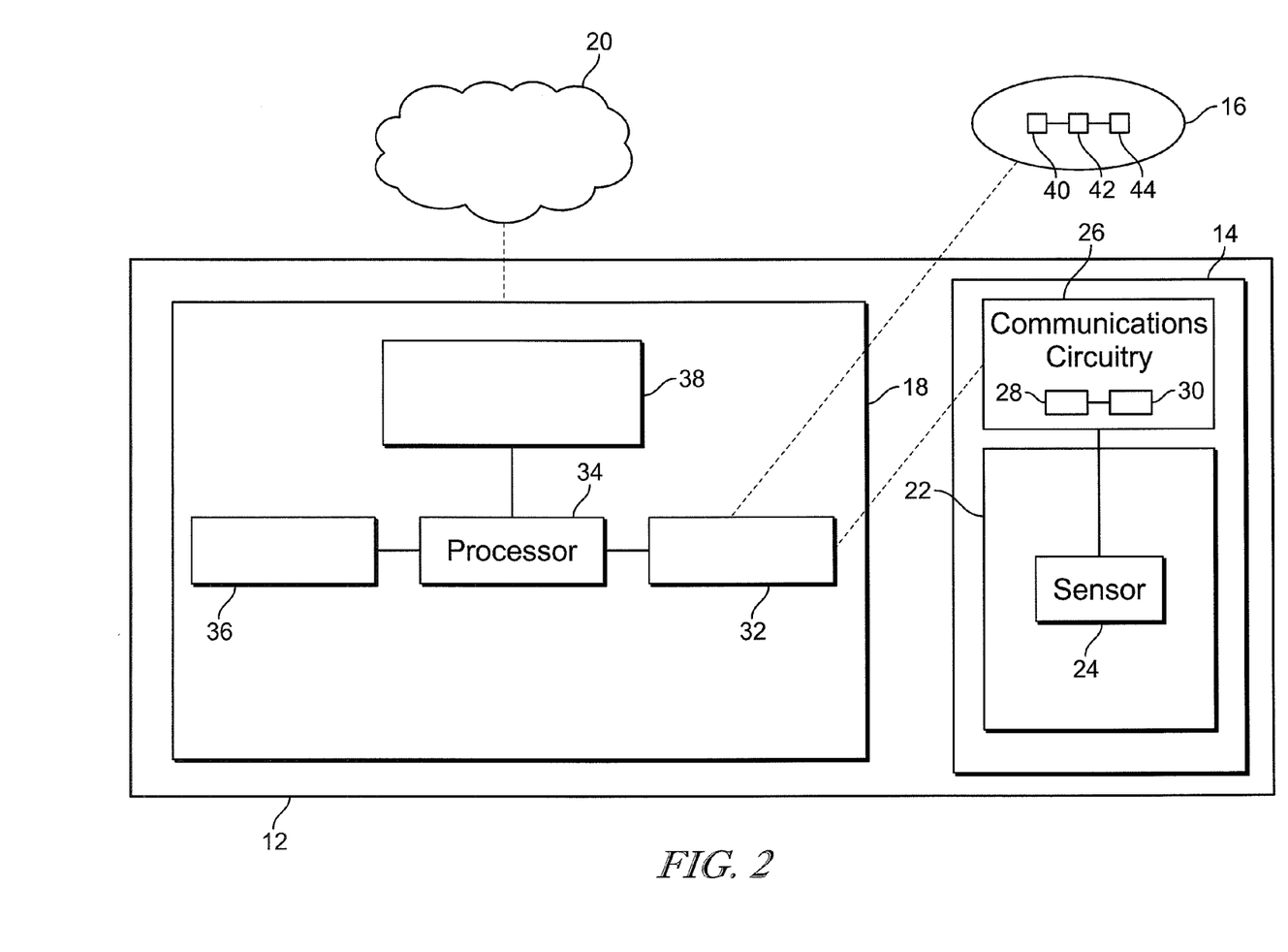
FIG. 2 is a diagrammatic view of the incontinence detection system of FIG. 1 showing various internal components of a communications device, the incontinence detection device, and the location transmitter, and showing that the communications device is in communication with a network of the care facility.

In the illustrative embodiment as shown in FIG. 2, the incontinence detection device 14 is embodied as an incontinence pad including a substrate 22, at least one sensor 24 mounted on the substrate 22 to sense the presence of moisture, and communications circuitry 26 communicating with the sensor 24 to receive an indication of moisture presence. The incontinence detection device 14, as an incontinence pad, is illustratively removable and replaceable for easy change out by caregivers and while permitting the new pad to automatically communicate wirelessly with the RFID reader 18 of the same patient bed 12 based on proximity. In some embodiments, upon change out by a caregiver, a new pad may be affirmatively linked to the RFID reader 18 by wireless and/or wired connection. The communications circuitry 26 generates an incontinence signal in response to the sensor 24 having sensed the presence of moisture for communication to the RFID reader 18.

In the illustrative embodiment, the communications circuitry 26 is embodied as a passive RFID device, but in some embodiments may include any number of passive, semi-active, and/or active RFID devices. The communications circuitry 26 is embodied to include at least a microchip 28 and an antenna 30 configured to receive radio frequency (RF) waves from the RFID reader 18 to power the microchip 28. In some embodiments, the communications circuitry 26 may include any variety of hardware and/or software to communicate incontinence detection to the communications device 18 (i.e., the RFID reader).

After occurrence of an incontinence event, RF waves from the RFID reader 18 that are transmitted periodically to interrogate circuitry 26, power the microchip 28 such that if the sensor 24 senses the presence of moisture, the microchip 28 generates an incontinence signal indicating the presence of moisture for communication to the RFID reader 18. If the sensor 24 does not sense the presence of moisture, the microchip 28 illustratively does not generate an incontinence signal regardless of any RF waves received from the RFID reader 18. Alternatively, in the absence of moisture on sensor 24 from an incontinence event, the data transmitted by circuitry 26 indicates the absence of moisture. By using RF-based communications to the RFID reader, the illustrative incontinence detection system 10 enables easy retrofitting to existing equipment and facilities, using components with low power demand as well as low cost incontinence detection design, for example, with the removable and replaceable incontinence pad, to provide location specific incontinence detection and monitoring.

In the illustrative embodiment, the incontinence detection device 14 has a predetermined moisture detection threshold at which to communicate the incontinence signal embodied as a sensing threshold of the sensor 24. In some embodiments, the predetermined moisture detection threshold may include a sensing threshold of the sensor 24, may be adjustable, may be a signal threshold determined by the microchip 28 and/or the RFID reader 18, and/or any combinations thereof.

In the illustrative embodiment as shown in FIG. 2, the RFID reader 18 communicates with the incontinence detection device 14, the location transmitter 16, and the network 20. The RFID reader 18 illustratively includes device communications circuitry 32 for communicating with each of the location transmitter 16 and the incontinence detection device 14, a processor 34, a memory device 36 storing instructions for execution by the processor 34, and a network communication module 38 including circuitry for communicating with the network 20. In the illustrative embodiment, the RFID reader 18 is connected to the on-board battery of the patient bed 12, but in some embodiments may include a dedicated power source. Alternatively or additionally, a power cord of bed 12 is plugged into an alternating current (AC) power outlet and reader 18 is powered from the AC power source via circuitry of bed 12.

In the illustrative embodiment, the RFID reader 18 generates and sends RF waves as an excitation signal at regular intervals to power the incontinence detection device 14 to transmit incontinence signals responsive to sensing the presence of moisture. The device communications circuitry 32 is illustratively embodied to include any number of antennas, receivers, transmitters, amps, modulators, demodulators, and/or other components, and/or combinations thereof arranged to communicate with active and passive RFID devices as directed by the processor 34. The device communications circuitry 32 illustratively powers the communications circuitry 26 of the incontinence detection device 14 and receives any incontinence signals generated therefrom.

In the illustrative embodiment, the location transmitter 16 is configured to communicate with the RFID reader 18. The location transmitter 16 is illustratively embodied as an active RFID device including at least a power source 40, a microchip 42 powered by the power source 40, and an antenna 44 for sending and receiving signals as directed by the microchip 42. In the illustrative embodiment, the power source 40 comprises a photovoltaic cell, but in some embodiments may include a battery, hardwired power from the care facility, any other suitable power source, and/or combinations thereof. In the illustrative embodiment, the location transmitter 16 is embodied as a beacon that transmits the location signal at regular intervals, but in some embodiments may comprise a transponder which receives a request (or activation signal) from one or more devices, for example, the RFID reader 18 to trigger the location transmitter 16 to send the location signal.

In the illustrative embodiment, the RFID reader 18 receives a location signal from the location transmitter 16 indicating a unique location identifier. The unique location identifier is illustratively embodied as an identification code associated with a particular location within the care facility as discussed in additional detail below. The RFID reader 18 illustratively receives the location signal from the location transmitter 16 and stores the indicated unique location identifier in the memory device 36 for retrieval. Upon receiving a new location signal, the RFID reader 18 illustratively updates the stored unique location identifier for retrieval.

When the RFID reader 18 receives an incontinence signal from the incontinence detection device 14, the RFID reader 18 illustratively retrieves the unique location identifier and sends a communications signal to the network 20. The communications signal illustratively indicates the unique location identifier and the occurrence of the incontinence event. In the illustrative embodiment, the communications signal is embodied to indicate a combined identification code generated by the RFID reader 18 and indicating the unique location identifier and the occurrence of the incontinence event. In some embodiments, the communications signal may include separate indicators, for example, separation identification codes, for each of the unique location identifier and the occurrence of the incontinence event.

In the illustrative embodiment, the RFID reader 18 illustratively sends the communications signal to the network 20. The network 20 illustratively receives the communications signal from the RFID reader 18 and alerts caregivers to the occurrence and location of the incontinence event. The network 20 illustratively includes a call system 46 including circuitry for communicating with RFID reader 18 and for conducting various other network communications (for example, communications with caregivers via local terminals and/or mobile devices), a database 48 embodied as a relational database for storing information and/or associating identifying information of the care facility (for example, staff, caregivers, patients, equipment, and locations), a server 50 for facilitating various network operations, and a user interface 52 for interacting with information on the network 20 and communicating over the network 20. An example of a suitable call system 46 may include the NaviCare® Nurse Call system marketed by Hill-Rom Company, Inc. In some embodiments, the network 20 may include any number and/or configuration of hardware and/or software components to perform network operations.

In the illustrative embodiment, the network 20 stores and maintains association of the unique location identifier with the location of the location transmitter 16 for retrieval. The database 48 illustratively stores and the unique location identifier with a predetermined location of the location transmitter 16 within the care facility, illustratively embodied as within room 100.

The network 20 illustratively receives the communications signal from the RFID reader 18, retrieves the predetermined location associated with the indicated unique location identifier and communicates to caregivers the occurrence and location of the incontinence event. In some embodiments, the predetermined location may be any known location including a particular sub-section of room 100. In some embodiments, the unique location identifier may correspond directly to the predetermined location and be received and communicated throughout the network 20 without requiring retrieval of its location association. In the illustrative embodiment, the network 20 communicates the occurrence and location of the incontinence event to caregivers by display on the user interface 52, but in some embodiments may include indication, via the call system 46, through screen indicators, lights, and/or alarms at various locations within the care facility, indication on a mobile device carried by one or more of the caregivers, and/or combinations thereof.

Figure 3:
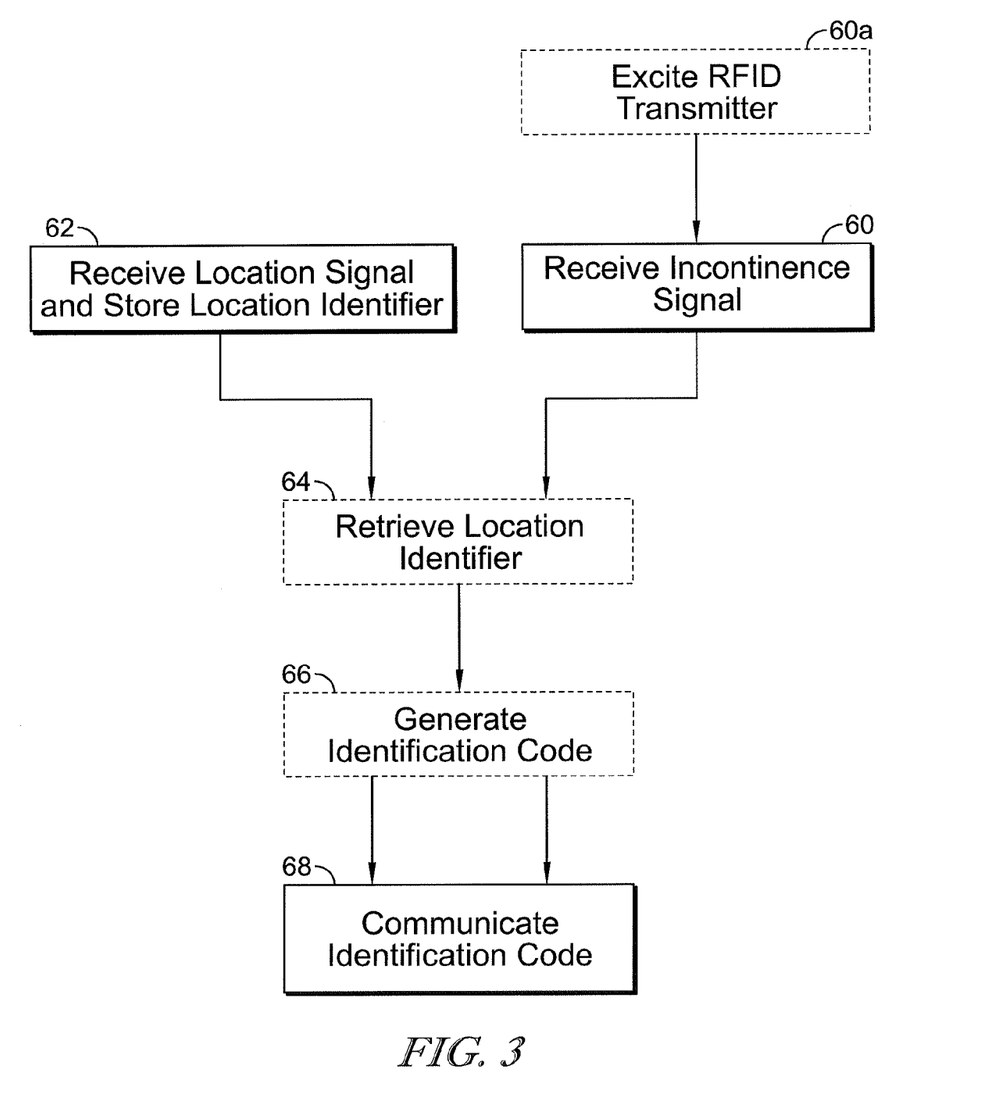
FIG. 3 is a process flow diagram of operation of the incontinence detection system of FIGS. 1 and 2.

Referring to FIG. 3, an illustrative process flow diagram is shown for detecting and monitoring incontinence event occurrence and location according to steps 60-68. In step 60, the RFID reader 18 receives an incontinence signal. As mentioned above, the RFID reader 18 illustratively receives the incontinence signal from the incontinence detection device 14 as a response to the sensor 24 having sensed the presence of moisture. In the illustrative embodiment, the communications circuitry 26 of the incontinence detection device 14 is a passive RFID device that is power by RF waves from the RFID reader 18. As indicated in step 60a, the RFID reader sends RF waves to power (excite) the incontinence detection device 14 to provide the applicable incontinence signal received in step 60.

In step 62, the RFID reader 18 receives the location signal. As mentioned above, the location transmitter 16 illustratively sends the location signal periodically as a beacon to the RFID reader 18 indicating the unique location identifier. The RFID reader 18 illustratively stores the unique location identifier for retrieval upon reception of an incontinence signal. In some embodiments, the RFID reader 18 may prompt the location transmitter 16 for a location signal in response to receiving the incontinence signal.

In step 64, the RFID reader 18 illustratively retrieves the stored unique location identifier in response to receiving the incontinence signal. In step 66, the RFID reader illustratively generates an identification code indicating the occurrence of an incontinence event and the unique location identifier.

In step 68, the RFID reader 18 communicates the identification code indicating the occurrence and location of the incontinence event to caregivers. The RFID reader 18 illustratively sends the communications signal indicating the occurrence of the incontinence event and the unique location identifier to the network 20 for communication to caregivers. In some embodiments, the communications signal may include an indication of any of the date, the time, the severity, and/or any other identifying information regarding the incontinence event.

In the illustrative embodiment, the RFID reader 18 communicates the communications signal to the network 20 for communication to caregivers, but in some embodiments the RFID reader 18 may communicate to any of local and/or remote devices and/or persons directly and/or indirectly. In some embodiments, in additional to, as a part of, and/or in place of communication with the network 20, the RFID reader 18 may communicate the communications signal to relatively local devices for direct communication to caregivers, for example, to a local user interface, and/or may communicate to intermediate communication devices as a communications relay to the network 20 and/or other devices.

In the illustrative embodiment, RFID communications, including passive, semi-active, and active, are embodied to use the same protocol, but in some embodiments may use any number and type of suitable protocols having appropriate conversion hardware and/or software as appropriate. In some embodiments, the communication device 18 may communicate with the incontinence detection device 14 and the location transmitter 16 by any suitable type of wired and/or wireless communication. The present disclosure includes hardware and/or software (including firmware) circuitry components and arrangements for conducting the communications functions as indicated herein.

The present disclosure includes devices, systems, and methods for detecting and communicating the occurrence and location of incontinence events without introduction of extensive additional hardware and/or software. This includes incontinence and location specific components which can be retrofitted to existing facilities and equipment while reducing the need for additional components and/or processes, for example, multipurpose components which can increase complexity and/or cost.

Although certain illustrative embodiments have been described in detail above, variations and modifications exist within the scope and spirit of this disclosure as described and as defined in the following claims.

We claim:

1. An incontinence detection system, comprising:
a patient bed,
an incontinence detection device positioned on the patient bed to detect incontinence events, the incontinence detection device including a sensor adapted to sense the presence of a threshold amount of moisture on the patient bed and to communicate a detection signal indicating the presence of the threshold amount of moisture and an RFID-incontinence transmitter in communication with the sensor and adapted to send an incontinence RFID signal indicating that the threshold amount of moisture has been sensed in response to the detection signal,
an RFID-location transmitter fixed relative to the patient bed and configured to send a location RFID signal indicating a unique location identifier, and
an RFID reader configured to receive the incontinence RFID signal and the location RFID signal, configured to generate an identification code indicating both an occurrence of the threshold amount of moisture as an incontinence event and the unique location identifier, and configured to send, responsive to an incontinence event, a communications signal indicating the identification code to at least one remote device in response to receiving the incontinence RFID signal and the location RFID signal.

2. The incontinence detection system of claim 1, wherein the RFID-incontinence transmitter comprises a passive RFID device.

3. The incontinence detection system of claim 2, wherein the passive RFID device receives excitation from the RFID reader to power the RFID-incontinence transmitter.

4. The incontinence detection system of claim 3, wherein the RFID reader is configured to transmit excitation signals at regular intervals to the RFID-incontinence transmitter to power the RFID-incontinence transmitter.

5. The incontinence detection system of claim 1, wherein the RFID-location transmitter comprises an active RFID device.

6. The incontinence detection system of claim 5, wherein the active RFID device includes a power source comprising a photovoltaic cell.

7. The incontinence detection system of claim 1, wherein the RFID reader is attached to the patient bed.

8. The incontinence detection system of claim 1, wherein the incontinence device comprises a removable and replaceable pad.

9. The incontinence detection system of claim 1, wherein the RFID reader is configured to send the communications signal indicating the identification code to at least one remote device via a nurse call system of a care facility.

10. The incontinence detection system of claim 1, wherein the threshold amount of moisture is a sensing threshold of the sensor.

11. The incontinence detection system of claim 1, wherein the sensor is configured to communicate an indication of no incontinence event when the threshold amount of moisture is absent.

12. An incontinence detection system, comprising:
an incontinence detection device for detecting incontinence events, the incontinence detection device including an incontinence pad and an RFID-incontinence transmitter, the incontinence pad including at least one sensor adapted to sense the presence of moisture and to communicate a detection signal indicating the presence of moisture to the RFID-incontinence transmitter, the RFID-incontinence transmitter being adapted to send an incontinence RFID signal indicating that moisture has been sensed in response to receiving the detection signal, an RFID-location transmitter fixed relative to a patient support device and configured to send a location RFID signal indicating a unique location identifier, and an RFID reader configured to receive the incontinence RFID signal and the location RFID signal, and configured to generate an identification code and to transmit an indication of the identification code as a communication signal, in response to receiving the incontinence RFID signal and the location RFID signal, wherein the identification code indicates both an occurrence of the presence of moisture as an incontinence event and the unique location identifier to at least one remote device.

13. The incontinence detection system of claim 12, wherein the RFID-incontinence transmitter comprises a passive RFID device.

14. The incontinence detection system of claim 13, wherein the passive RFID device receives excitation from the RFID reader to power the RFID-incontinence transmitter.

15. The incontinence detection system of claim 14, wherein the RFID reader is configured to transmit excitation signals at regular intervals to the RFID-incontinence transmitter to power the RFID-incontinence transmitter.

16. The incontinence detection system of claim 12, wherein the RFID-location transmitter comprises an active RFID device.

17. The incontinence detection system of claim 16, wherein the active RFID device includes a power source comprising a photovoltaic cell.

18. The incontinence detection system of claim 12, wherein the RFID reader is attached to the patient support device.

19. The incontinence detection system of claim 12, wherein the incontinence pad comprises a removable and replaceable pad.

20. The incontinence detection system of claim 12, wherein the RFID reader is configured to transmit the communications signal over a nurse call system of a care facility.

21. A method of detecting an incontinence event on a patient support device having an RFID reader, comprising:
    receiving with the RFID reader a location RFID signal indicating a unique location identifier and storing the unique location identifier,
    receiving with the RFID reader an incontinence RFID signal indicating the presence of moisture, and
    in response to receiving the incontinence RFID signal, generating an identification code indicating an occurrence of an incontinence event and the unique location identifier, wherein generating the identification code includes retrieving the unique location identifier from storage, and transmitting a communications signal indicating the identification code.

22. The method of detecting an incontinence event of claim 21, further including receiving at least one excitation signal for powering a passive RFID transmitter, including receiving an excitation signal from the RFID reader at regular intervals.

* * * * *

UNITED STATES PATENT AND TRADEMARK OFFICE
CERTIFICATE OF CORRECTION

PATENT NO. : 10,115,291 B2  
APPLICATION NO. : 15/490109  
DATED : October 30, 2018  
INVENTOR(S) : Dan R. Tallent et al.

Page 1 of 1

It is certified that error appears in the above-identified patent and that said Letters Patent is hereby corrected as shown below:

On the Title Page

Item (56) References Cited, Page 2, under the heading U.S. PATENT DOCUMENTS, please replace the name "Zibetin" in the line for U.S. Patent No. 5,675,854 with --Zibelin--.

Signed and Sealed this  
Nineteenth Day of February, 2019

Andrei Iancu  
*Director of the United States Patent and Trademark Office*